US012329496B2

(12) United States Patent
Wilson et al.

(10) Patent No.: US 12,329,496 B2
(45) Date of Patent: Jun. 17, 2025

(54) SPECTRAL ANALYSIS OF A SAMPLE

(71) Applicant: Agilent Technologies LDA UK Limited, Cheadle (GB)

(72) Inventors: Philip Valmont Wilson, Mount Waverly (AU); William Parker, Oxford (GB); Joao Mendes-Lopes, Lisbon (PT)

(73) Assignee: Agilent Technologies LDA UK Limited, Cheadle (GB)

( * ) Notice: Subject to any disclaimer, the term of this patent is extended or adjusted under 35 U.S.C. 154(b) by 290 days.

(21) Appl. No.: 17/925,272

(22) PCT Filed: Mar. 2, 2021

(86) PCT No.: PCT/GB2021/050520
§ 371 (c)(1),
(2) Date: Nov. 14, 2022

(87) PCT Pub. No.: WO2021/229201
PCT Pub. Date: Nov. 18, 2021

(65) Prior Publication Data
US 2023/0218174 A1    Jul. 13, 2023

(30) Foreign Application Priority Data

May 14, 2020 (GB) ...................................... 2007136

(51) Int. Cl.
*A61B 5/00* (2006.01)
*G01J 3/02* (2006.01)
(Continued)

(52) U.S. Cl.
CPC .......... *A61B 5/0075* (2013.01); *G01J 3/0205* (2013.01); *G01J 3/0208* (2013.01); *G01J 3/0216* (2013.01);
(Continued)

(58) Field of Classification Search
CPC .... A61B 5/0075; G01J 3/0205; G01J 3/0208; G01J 3/0216; G01J 3/0221; G01J 3/0229;
(Continued)

(56) References Cited

U.S. PATENT DOCUMENTS

| 5,112,125 A | 5/1992 | Neumann |
| 6,870,619 B1 * | 3/2005 | Tenhunen ................. G01J 3/28 |
| | | 356/330 |

(Continued)

FOREIGN PATENT DOCUMENTS

| CN | 106705856 A | 5/2017 |
| CN | 110208294 A | 9/2019 |

OTHER PUBLICATIONS

PCT, "Notification of Transmittal of The International Search Report & Written Opinion mailed on May 18, 2021," Application No. PCT/GB2021/050520, 17 pages.
(Continued)

*Primary Examiner* — Dominic J Bologna

(57) ABSTRACT

Apparatus and methods for spectral analysis of a sample are described, for example for carrying out Raman or other optical or spectroscopic analysis of samples such as pharmaceutical dosage forms, including oral solid dosage forms such as tablets or capsules. Such apparatus may comprise delivery optics arranged to direct probe light to a delivery region of the sample, collection optics arranged to collect probe light scattered from a collection region of the sample, and a spectrometer having an entrance port, the spectrometer being arranged to receive the collected probe light from the collection optics at the entrance port of the spectrometer, and to detect spectral features in the received probe light. In particular, the collection optics may comprise Koehler integration optics arranged to process the collected probe light such that the collected light from each point of the collection
(Continued)

region is distributed across the entrance port of the spectrometer.

19 Claims, 9 Drawing Sheets

(51) Int. Cl.
| | |
|---|---|
| *G01J 3/44* | (2006.01) |
| *G01J 3/45* | (2006.01) |
| *G01J 3/453* | (2006.01) |
| *G01N 21/31* | (2006.01) |
| *G01N 21/3563* | (2014.01) |
| *G01N 21/47* | (2006.01) |
| *G01N 21/65* | (2006.01) |
| *G01N 21/95* | (2006.01) |
| *G01N 33/15* | (2006.01) |

(52) U.S. Cl.
CPC ............ *G01J 3/0221* (2013.01); *G01J 3/0229* (2013.01); *G01J 3/0289* (2013.01); *G01J 3/0297* (2013.01); *G01J 3/44* (2013.01); *G01J 3/4412* (2013.01); *G01J 3/45* (2013.01); *G01N 21/31* (2013.01); *G01N 21/474* (2013.01); *G01N 21/9508* (2013.01); *G01N 33/15* (2013.01); *G01J 2003/4538* (2013.01); *G01N 21/3563* (2013.01); *G01N 2021/4735* (2013.01); *G01N 2021/4745* (2013.01); *G01N 21/65* (2013.01)

(58) Field of Classification Search
CPC .......... G01J 3/0289; G01J 3/0297; G01J 3/44; G01J 3/4412; G01J 3/45; G01J 2003/4538; G01N 21/31; G01N 21/474; G01N 21/9508; G01N 33/15; G01N 21/3563; G01N 21/65; G01N 2021/4735; G01N 2021/4745
See application file for complete search history.

(56) References Cited

U.S. PATENT DOCUMENTS

| | | | |
|---|---|---|---|
| 2005/0006590 A1* | 1/2005 | Harrison | G01J 3/0208 250/372 |
| 2008/0151225 A1 | 6/2008 | Treado et al. | |
| 2011/0071055 A1* | 3/2011 | Belgrader | B01L 3/502715 422/68.1 |
| 2012/0035442 A1 | 2/2012 | Barman et al. | |
| 2014/0093977 A1* | 4/2014 | Raphael | G01N 21/554 422/69 |
| 2015/0103229 A1 | 4/2015 | Nozawa | |
| 2015/0355082 A1* | 12/2015 | Lu | G01N 33/0031 356/437 |
| 2019/0017808 A1 | 1/2019 | Kimba | |
| 2019/0064072 A1* | 2/2019 | Kim | G01J 3/0218 |

OTHER PUBLICATIONS

Raphael, Marc P. et al., "Quantitative LSPR Imaging for Biosensing with Single Nanostructure Resolution," Biophysical Journal, vol. 104, No. 1, Jan. 1, 2013, 30-36.

Uwevogler, Vogler et al., "Mask Aligner Process Enhancement by Spatial Filtering," Illumination Optics II, SPIE, vol. 8170, No. 1, Sep. 22, 2011, 1-8.

* cited by examiner

SPECTRAL ANALYSIS OF A SAMPLE

CROSS-REFERENCE TO RELATED APPLICATION

This application is a U.S. National Stage Entry of International Application No. PCT/GB2021/050520, filed on Mar. 2, 2021, which claims priority from Great Britain Application No. 2007136.1, filed May 14, 2020, the contents of which are incorporated by reference in their entirety.

The present invention relates to apparatus and methods for carrying out Raman or other optical or spectroscopic analysis of samples such as pharmaceutical dosage forms, including oral solid dosage forms such as tablets or capsules. For example, such dosage forms or other samples may be analysed using Raman spectroscopy in a transmission configuration.

INTRODUCTION

In various situations such as production line sampling it is desirable or necessary to test pharmaceutical dosage forms to check compliance with particular specifications. Such specifications may define narrow acceptable ranges of absolute content of one or more active pharmaceutical ingredients (APIs), as well as other aspects such as shape, size, and content of other chemical components and properties of the dosage form.

One way of determining such content and chemical properties is to separately grind each sample dosage form to a powder, dissolve in a solvent, and introduce to a liquid chromatograph, mass spectrometer or similar device. However, when large numbers of dosage forms need to be individually tested this process can be slow and difficult to automate effectively. Difficulties of accurately tracking the identity of each dosage form sample through such an analysis process arise, and physical properties and identifying markings of the original dosage form are lost in the process.

Spectroscopic testing of pharmaceutical dosage forms for quantitative analysis is described for example in PCT/SE96/01637, and WO2007/113566. Dosage forms may take the form of tablets, capsules and other formulations. However, carrying out such spectroscopic testing in a consistent manner across a plurality of similar such samples can be challenging, with even apparently identical samples sometimes giving sufficiently different results to be of concern.

The invention seeks to address problems and limitations of the related prior art.

SUMMARY OF THE INVENTION

Typical spectroscopic systems, for example Raman systems, use an imaging lens system to couple light from the sample onto the input to a spectrometer, either directly onto the spectrometer port, or by imaging onto the input face of an optical fibre bundle. This means that the distribution of light at the input to the spectrometer contains spatial information relating to the sample morphology. In many situations, however, it may be desirable to sample a volume or bulk of a sample, or to otherwise carry out spectroscopic analysis which is insensitive to a precise position, orientation or movement of the sample, and which can therefore also provide improved consistency of spectroscopic analysis between multiple similar samples.

Spectroscopic variations arising from variations in position, orientation or movement of the sample can take the form of intensity fluctuations or peak shifts. Intensity fluctuations may take place in backscatter configurations due to changes in sample face angle relative to collection optics and illumination, and changes in position of surface features. For transmission configurations, even small changes in sample orientation and position can lead to different optical path lengths and geometries through the sample, especially if the sample is of varying thickness, or contains surface or subsurface features.

Shifts in the positions of spectral peaks can occur because intensity fluctuations can create differences in the angular input of light into the spectrometer. Spectrometers where the slit is illuminated directly by light from the sample may be most susceptible to this effect, but systems where light is carried to the slit by optical fibres are not immune, especially when the numerical apertures of the optical fibres are higher than that of the spectrometer.

The invention therefore addresses issues with the angular and spatial variances in light from a sample being introduced to a spectrometer. If the samples are pharmaceutical dosage forms such as a plurality of similar or essentially identical tablets or capsules, which frequently include embossed or debossed patterns or other surface markings as well as geometric structure, small variations position or orientation of these dosage forms can affect the distribution of light entering the spectrometer, leading to inconsistencies in spectral measurements and therefore determination of properties between the plurality of such samples.

To this end, the invention provides apparatus for spectroscopic analysis of samples which includes Koehler integration optics, so as to spread collected light from the sample in a uniform manner independent of the geometry of the sample. This is achieved by imaging an intermediate plane and projecting this distribution. This ensures that spatial information from the sample surface is not coupled into the input to the spectrometer. This does not necessarily eliminate far-field variances, although these can be addressed using a "fly's-eye" lenslet array configuration of Koehler optics where a pair of matched lenslet arrays are used to subsample the intermediate aperture. This ensures that all spatial and angular information is averaged out to provide very uniform near and far field distributions of light.

This means that light from each position on the sample surface is distributed over all fibres of an optical fibre bundle carrying the light to the spectrometer, or distributed over the whole of the input light into the spectrograph, instead of one optical fibre or one part of the spectrograph port corresponding to one location or region of the sample surface. Even if just a single optical fibre is used to carry light to the spectrometer, rather than a bundle of optical fibres, use of the invention provides a better distribution of the light from the sample surface into that single optical fibre.

Shifts in position of samples and any surface features relative to the optics used to collect the light will then then have a much reduced influence on the structure of the light entering the spectrometer. Moreover, all optical fibres and/or portions of the spectrometer port then carry the same spectral information, facilitating more advanced modes of analysis of spectral data detected at the spectrometer.

Aspects of the invention therefore provide methods and apparatus for spectral analysis of a sample, in which collection optics collect probe light from the sample, and a spectrometer receives the collected probe light from the collection optics, wherein the collection optics comprise Koehler integration or integrator optics which process the collected probe light before it is passed to the spectrometer. In particular, the Koehler integration optics may operate such that the collected light from each point of the collection region is distributed across most or all of the spatial extent of the light received at the spectrometer.

However, other, different optical arrangements many instead be used to process the light collected from the sample to reduce or remove spatial sample image information from the collected light before being input to the spectrometer. For example, optics such as compound hyperbolic concentrators, or non-imaging concentrator lenses could instead be used to process collected light in a way that does not preserve the spatial information of the sample at the input plane or port of the spectrometer.

More particularly, aspects of the invention provide apparatus for spectral analysis of a sample, comprising: delivery optics arranged to direct probe light to a delivery region of the sample; collection optics arranged to collect probe light scattered from a collection region of the sample; and a spectrometer having an entrance port, the spectrometer being arranged to receive the collected probe light from the collection optics at the entrance port of the spectrometer, and to detect spectral features in the received probe light, wherein the collection optics comprise Koehler integration optics, or other non-imaging optics arranged to have a similar effect. The Koehler integration optics other non-imaging optics may be described as being arranged to process the collected probe light such that the collected light from each point of the collection region is distributed across the entrance port of the spectrometer.

The sample may typically be a solid sample, so that the delivery and collection regions are regions on one or more surfaces of the sample. Different geometries and locations of the delivery and collection regions may be used to implement different geometries of optical analysis of the sample, for example in backscatter and transmission geometries.

The apparatus may further comprise one or more suitable light sources to generate said probe light for directing at the sample, for example one or more infrared lasers. The apparatus may further comprising an analyser arranged to determine one or more properties of the sample from the detected spectral features, such as the presence or measured content of particular chemical species within or at the surface of the sample.

The apparatus may implement Raman spectroscopy of the sample, such that the detected spectral features are or include Raman spectral features such as the magnitudes of one or more Raman spectral peaks, from which properties of the sample can be determined.

The collection optics may comprises a bundle of two or more optical fibres (or a single optical fibre in some embodiments) having an entry face arranged to receive the collected probe light following processing by the Koehler integration optics, and an exit face arranged to deliver the collected probe light to the port of the spectrometer, which may typically be a slit of the spectrometer.

Although in some geometries for analysing the sample, the delivery and collection regions may be coincident or overlapping so as to effect a backscatter geometry, in others the collection region may be spaced from the delivery region. In particular, the collection region may be on an opposite side of the sample from the delivery region, such that light is collected from the collection geometry following forward scattering within the sample, under a transmission geometry.

Typically the Koehler integration optics may comprise a collector arranged to receive the collected light from the collection region of the sample, and a condenser arranged to receive the collected light from the collector. Each of the collector and condenser may comprise one or more simple or compound lenses, and these may be of spherical or aspherical form as required.

The Koehler integration optics may then include or define an intermediate plane at or proximal to the collector, and an output plane, the collector being arranged to form an image of the collection region of the sample at or proximal to the condenser, and the condenser being arranged to form an image of the intermediate plane at the output plane.

In such contexts, the term proximal may mean for example that the image of the collection region is formed within +−10% of the distance from an optical centre or optical element of the collector to an optical centre or optical element of the condenser, and/or that the intermediate plane is located within +−10% of the distance from an optical centre or optical element of the condenser to an optical centre or optical element of the collector. A similar interpretation of proximal may be used in other contexts. The term proximal is used because exact positioning of elements, images and so forth may be desirable for optimal functioning of the Koehler integration optics, but may not be strictly necessary for adequate performance so as to still function as Koehler integration optics as would be understood by the skilled person.

The collection optics may comprise an optical fibre, or more usually a bundle of optical fibres, the fibre or bundle having an entry face arranged to receive the collected probe light following processing by the Koehler integration optics, and an exit face arranged to deliver the collected probe light to the port of the spectrometer. The output plane of the Koehler integration optics mentioned above may then be located at or proximal to the entry face.

The collection optics may comprise one or more groups of collimator lenses and one or more spectral filters disposed within each group of collimator lenses, each group of collimator lenses being arranged such that the collected light is collimated when passing through the one or more spectral filters disposed within the group. The collimation permits improved operation of the spectral filters, in particular if the spectral properties of the spectral filters are dependent on angle of incidence, for example if multilayer dielectric (interference) filters are used. To this extent, the degree of collimation provided by the collimation lenses may be only moderate, for example with 90% of the collected light being within 10 degrees or within 20 degrees of the optical axis of the collection optics or Koehler integration optics A said group of collimator lenses may be lenses of the collector and one or more said spectral filters may then be comprised within or may provide the collector.

Additionally or instead, a said group of collimator lenses may be comprised in or provide an output relay arranged to relay an image of the output plane from the condenser, and one or more said spectral filters may then be comprised within the output relay.

Additionally or instead, a said group of collimator lenses may be comprised in or define a sample relay arranged to form a relayed virtual image of the collection region for imaging by the collector, and one or more said spectral filters are comprised within the sample relay. A sample diaphragm may be provided between the sample relay and the collector, the sample relay being arranged to form the relayed virtual image of the collection region at the sample diaphragm.

As noted above, the detected spectral features may be Raman spectral features, which are defined in terms of wavenumber offsets from one or more probe wavelengths of the probe light directed to the delivery region of the sample. The one or more spectral filters may then comprise spectral filters arranged to block light of the original probe wavelengths but to allow light of the Raman spectral features to pass.

The apparatus may further comprise a sample diaphragm, and a sample relay arranged to form a relayed virtual image of the collection region at the sample diaphragm for imaging by the collector.

The apparatus may further comprise a condenser diaphragm at or proximal to the condenser, such that the condenser diaphragm constrains the extent of the virtual image of the collection region formed by the collector at or proximal to the condenser.

In some arrangements, the collector may comprise a collector lenslet array, and the condenser may comprise a corresponding or matching condenser lenslet array. These lenslet arrays may be co-focal, that is they may be mutually located at the other's focal distance. The lenslet arrays can thereby be arranged to subsample the apertures of the collector and condenser. These subsamples are then superimposed at the output plane, further reducing the degree of spatial image information of the collection region in the processed, collected light.

A variety of different samples may be analysed using the described apparatus and methods, but in some embodiments the sample may be a pharmaceutical dosage form, for example one or more of: a tablet; a coated tablet; a capsule; and a gelcap, and may comprise one or more of: surface markings; debossing; embossing; a plurality of surface regions each having a different colour; and printed markings.

The transmission geometry described may in particular be used to determine properties of the bulk of such a pharmaceutical dosage form, with the use of Koehler integration optics in the collector minimising spectroscopic artefacts arising from slight differences in alignment or orientation of each of a plurality of similar such dosage forms, thereby providing improved consistency of analysis between the plurality of dosage forms.

The invention also provides methods corresponding to implementation and operation of the described apparatus, for example a method of spectral analysis of a sample, comprising: directing probe light to a delivery region of the sample; collecting probe light from a collection region of the sample; processing the collected probe light such that the collected light from each point of the collection region is distributed across the entrance port of the spectrometer; and delivering the processed collected probe light to the entrance port of a spectrometer.

For example, processing the collected probe light may comprise applying Koehler integration, or another de-imaging process, to the collected probe light.

The method may typically comprise the spectrometer detecting one or more spectral properties of the collected and processed light, and determining one or more properties of the sample from the detected spectral properties. In particular, the one or more spectral properties are Raman spectral properties.

The sample may be a pharmaceutical dosage form. A transmission geometry may be used to help determine properties of the bulk the dosage form, wherein the delivery region is on an opposite side of the sample from the collection region, or at least spaced from the collection region.

BRIEF SUMMARY OF THE DRAWINGS

Embodiments of the invention will now be described, by way of example only, and with reference to the drawings of which.

DETAILED DESCRIPTION OF PREFERRED EMBODIMENTS

Figure 1:
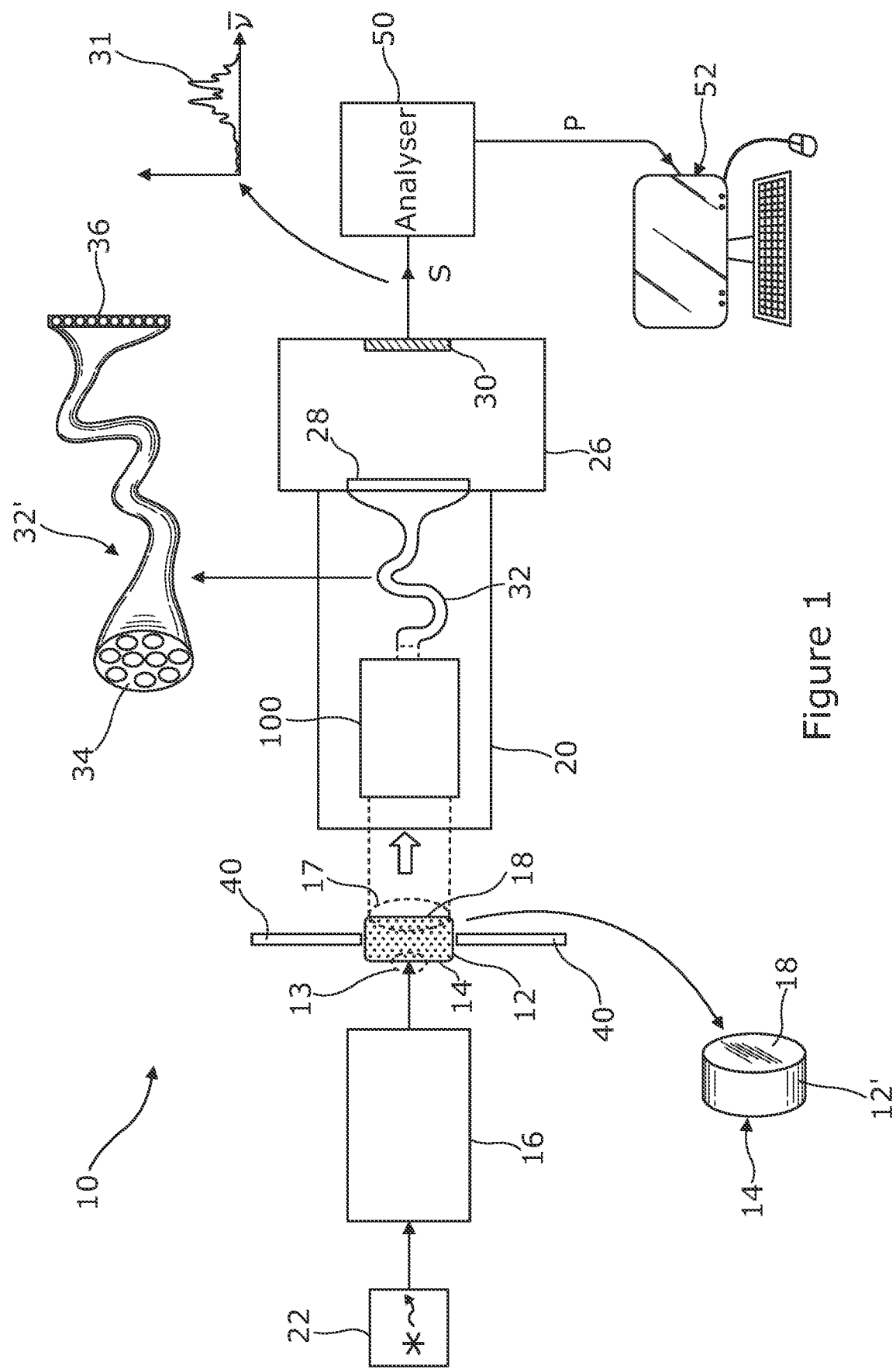
FIG. 1 shows schematically apparatus for spectral analysis of a sample such as a pharmaceutical dosage form, arranged in a transmission geometry.

Referring to FIG. 1, there is shown schematically apparatus 10 for spectral analysis of a sample 12 such as a pharmaceutical dosage form, which could for example be an oral solid dosage form such as a tablet or capsule, although other types of dosage forms or indeed other kinds of objects altogether may be analysed using apparatus and techniques described herein.

The apparatus 10 is arranged and operated to provide improved consistency of spectral or other optical analysis across a plurality of similar samples 12, for example across a batch of pharmaceutical dosage forms which are intended to be substantially identical. Dosage forms of such a batch may typically be superficially identical or very similar, for example in terms of shape, size and composition, but may still comprise defects and/or variations especially in internal chemical content and composition. It may be important to detect such defects and variations as part of a manufacturing process or other test scenario.

Pharmaceutical tablets are manufactured in a variety of shapes, sizes and colours. Some tablets may be of multiple different colours. Tablet shapes include cylindrical or elliptical prism forms, often with bevelled edges, spherical, ovoid, lozenge forms and so forth. Tablets are frequently embossed or debossed with markings such as alphanumeric codes and other symbols, slots to assist breaking into parts, and other surface features. Some tablets carry printed surface markings, for example including alphanumeric codes and other symbols. Tablets are manufactured both in coated forms in which a surface layer comprises different components to an underlying tablet core, and in uncoated forms.

Pharmaceutical capsules, of which gel capsules are one particular form, typically comprise an encapsulating sleeve containing pharmaceutical powders or sometimes gels or fluids. A typical shape for a capsule is cylindrical with rounded ends, but other geometries are sometimes used, for example flattened cylindrical forms. The encapsulating sleeve is typically formed by joining two opposing end sections, which are frequently of different colours. Capsules are often printed with surface markings such as alphanumeric codes and other symbols.

The inventors have found that various physical features of dosage forms such as those mentioned above can affect the consistency of results of optical analysis between a number of such dosage forms of the same type or batch even if these are superficially identical. It has been determined that consistency may be reduced for example if such dosage forms are presented for optical analysis in different orientations, rotational states or positions of those features with respect to the optical analysis equipment. Very few dosage forms which it might be desirable to analyse optically are essentially devoid of any such features or asymmetries.

The apparatus illustrated in FIG. 1 can be used as part of equipment providing automatic and sequential optical analysis of a plurality of samples such as a plurality of superficially identical or similar dosage forms, to provide improved consistency of optical analysis. Typical application areas may be for monitoring chemical composition properties of dosage forms sampled from a production line or other manufacturing process. Determined properties of the dosage forms may include measurements or concentrations or quantities of one or more active ingredients or other components, as well as measurements or concentrations or quantities of polymorph forms, hydrated forms, solvate forms, salt forms, and degrees of crystallinity of one or more such active ingredients or components. The presence or concentration of impurities may similarly be detected.

The apparatus illustrated in FIG. 1 is particularly arranged to carry out Raman spectral analysis of samples 12 such as pharmaceutical dosage forms, although other types of spectral or more generally optical analysis could also or instead be implemented. The mode of operation of the apparatus illustrated in FIG. 1 is one of transmission Raman spectroscopy, in which probe light is delivered to an delivery region 13 on a first surface 14 of the sample 12 by delivery optics 16, and elements of the probe light which have been forward scattered through the sample 12 are collected from a collection region 17 on a second surface 18 of the sample by collection optics 20 for detection of Raman scattered elements in the collected light. Such transmission Raman techniques are described for example in WO2007/113566, the contents of which are incorporated by reference for all purposes, and more particularly for describing ways in which transmission Raman techniques may be implemented.

Generally, in a transmission configuration, the second surface 18 may be spaced from the first surface 14 in such a manner that forward scattering brings Raman scattered elements of the probe light to the second surface to be collected and detected, so that the sample is analysed in a transmission or forward scattering geometry. Although different arrangements are possible, in FIG. 1 the second surface 18 is on an opposite side of the sample to the first surface 14. An example of this is illustrated for a tablet dosage form sample 12' shown in expanded view in FIG. 1, in which the first surface 14 is a first largely flat surface of the tablet dosage form 12', and the second surface 18 is a second largely flat surface of the tablet dosage form 12' which is opposite the first surface 14. For some dosage forms and more commonly for tablet forms, each of the first and second surfaces may be substantially parallel, often circular, and spaced from each other by a sidewall, and such that the dosage form has a generally rectangular cross section as seen in the main part of FIG. 1.

The shapes and sizes of the delivery and collection regions 13, 17 may be chosen according to need and design. Typically, in a transmission geometry arrangement such as that of FIG. 1, the delivery region may be a circular or elliptical region which is around 1-10 mm in diameter, and the collection region may be a circular or elliptical region which is of a similar size. The delivery region need not be a contiguous region, but could be made up of a plurality of separated areas, and the same is so for the collection region.

The apparatus of FIG. 1 comprises a laser light source 22 arranged to generate a beam of probe light, typically of infrared laser light, which the delivery optics 16 direct to the sample 12. The collection optics 20 are arranged to receive probe light following forward scattering, including Raman scattering, within the sample 12, and to deliver the collected probe light to a spectrometer 26.

Typically, the spectrometer 26 may be a dispersive spectrometer, such as a Kaiser Optical Technologies Holospec device. The collection optics deliver the collected probe light to an entrance port 28 of the spectrometer 26. The entrance port 28 may typically be a slit with a width chosen to provide a suitable compromise between light gathering and spectral resolution, and a length related to a size of an imaging component 30. However, other forms of a port may be used such as a binary coded port.

Spectral features S of the collected probe light, and in particular Raman spectral features, may then be detected by a CCD or other imaging component 30 forming part of the spectrometer 26. The detected Raman spectral features S, illustrated using a small graph in FIG. 1, may then be passed in the form of electronic data from the spectrometer 26 to an analyser 50 for further processing and use. The Raman spectral features 31, and/or further data derived from the spectral features may then be passed to other entities such as a locally connected personal computer 52, over one or more data networks, or stored on a data carrier for future use.

For convenience and flexibility of construction the collection optics typically comprise an optical fibre bundle 32, or sometimes just a single optical fibre, which carries the collected light to the spectrometer 26, typically to the entrance port 28. In FIG. 1 the optical fibre bundle is also illustrated as bundle 32' in expanded view, in which it can be seen that the optical fibre bundle may present an entry face 34 in which the ends of the separate optical fibres are clustered in a substantially circular envelope, for example being hexagonally close packed of similar, and an exit face 36 in which the ends of the separate optical fibres are distributed along an elongate envelope, for example in a single line. In this way, light collected from the second surface of the dosage form 12 can easily be projected onto the entry face 34 of the fibre bundle 32 using other parts of the collection optics, and can easily be directed into an elongate entry port or slit 28 of the spectrometer 26 by the exit face 36.

Typically, the laser light source 22 may operate in the near infrared, for example around 700 nm to 1000 nm, either as a continuous wave or pulsed source laser. Suitable average optical output power delivered to the sample 12 may be around 50 to 1200 mW, and a suitable spot diameter of the probe light beam at the sample 12 may be in the region of around 1 to 10 mm. Particularly small spot sizes may be avoided due to risks of heating or optical damage to the sample under test.

When implementing Raman spectral techniques, the collection optics 20 are usually designed to incorporate very good suppression of the wavelength band (i.e. fundamental wavelength) of the probe light as emitted by the laser source 22. Raman scattering cross sections are very small, so without such suppression the fundamental wavelength is likely to adversely affect accurate detection of the Raman spectral features, even though these may be spaced by tens of nanometers or more in wavelength from the laser wave band. This suppression may be achieved using one or more optical filters such as holographic notch or low pass filters within the collection optics 20 to suppress the laser waveband light which has been elastically scattered off, through or around the sample to be tested, as discussed in more detail below.

During optical analysis, the sample 12 may be supported or held in various ways by a support 40. For example, support 40 maybe provided by frame within which the sample rests or is held, by jaws of a robot manipulator or in other ways. Suppression of the laser waveband light in the collection optics 20 when detecting Raman spectral features 33 reduces the need to avoid stray probe light reflecting or scattering around the sample 12 and into the collection optics, as would usually be necessary if using infrared absorption spectroscopy and some other spectroscopic techniques. As a result, in many implementations the sample 12 to be tested may be suspended by the support 40 without particular need for an optical seal around the sides of the sample between the delivery optics 26 and collection optics 30 to prevent such stray light.

The analyser 50 may be arranged to determine one or more properties P of the sample 12 from the Raman spectral features 31 provided by the spectrometer 26, such as the various chemical properties mentioned above. For example, the analyser 34 may be arranged to detect aspects such as the magnitudes of particular Raman spectral peaks and other features which represent particular chemical components expected or looked for in the sample under test, broader spectral matches to spectra or multiple spectral features of such components, and so forth, for example with reference to one or more data libraries defining expected spectra and/or particular spectral features of such components.

Spectral data S and/or determined properties P of the tested sample may be used in various ways, for example being stored locally and/or remotely, transmitted across a network, further analysed, used to control a process such as a manufacture process used to create the sample under test, and so forth. In FIG. 1 the local personal computer 52 is shown as receiving the determined properties P, and may for example provide output of aspects of the determined properties to a person monitoring the apparatus 10, for example in the form of displays of deviations of determined properties from expected values, audible or visible alerts to bring the attention of such a person to sufficiently significant deviations, and so forth.

In the transmission arrangement of FIG. 1, the Raman spectral features S output by the spectrometer 26 can be detected as an average or other representative data set for the sample as a whole, at least to the extent that the whole sample is represented in the collected light. Indeed, the transmission Raman technique illustrated in FIG. 1 is particularly good at sampling the bulk of a sample such as a dosage form, with collected light carrying Raman spectral features arising from a broad volume within the sample. In this way the determined properties P can be properties of a dosage form or other sample as a whole and consistently comparable between tested dosage forms or other samples.

However, the inventors have found that such consistency is hard to achieve to the high degree of accuracy required in areas such as manufacture and testing of samples such as pharmaceutical dosage forms. It appears that various asymmetries and features of a dosage form or other sample under test, such as overall shape, surface, colour features, debossing and embossing, and printed markings, in conjunction with slight variations in the positioning of the sample under analysis including potentially small deviations in the positions or geometries of surface regions of the sample to which probe light is directed and from which scattered light is collected for analysis, lead to related deviations in intensity at positions across the entrance port 28 of the spectrometer 26, both as a function of position for example along the length of a spectrometer slit, and in terms of angular distribution.

As a consequence, the detected intensity of Raman spectral features such as peaks can vary slightly depending on the precise positioning and alignment of the sample under test. Then, because practical spectrometers also display slight shifts in apparent detected wavelength as well as detected intensity depending on the spatial and angular distributions of collected light at the entrance port or slit, the detected spectral position of Raman spectral features such as peaks can also vary slightly depending on the precise positioning and alignment of the dosage form under test.

These deviations in intensity and spectral position of spectral features S output by the spectrometer tend to be more significant if the collected light is projected directly at the spectrometer entrance port 28, but are still of sufficient magnitude to be of concern even when the collected light is carried to the entrance port 28 by an optical fibre or bundle of optical fibres 32 as illustrated in FIG. 1, especially if the numerical aperture of the fibre or bundle is higher than that of the spectrometer 26.

The collection optics 20 of FIG. 1 therefore comprises de-imaging optics, or more specifically Koehler integration optics 100, which operate to remove image structure from the light collected from the sample 12 in transmission of this light to the entrance port 28 of the spectrometer 26. By removing such image structure, variations in position or orientation of the sample with respect to the collection optics have less effect on the distribution of light across the spectrometer port. This process can be described in various ways, for example as processing the collected light such that the collected light from each point of the collection region is distributed across most or all of the entrance port of the spectrometer. In this respect, each point of the collection region may ideally contribute equally to each part of the light entering the entrance port, but of course this complete level of de-imaging is not required in order to provide a useful level of image information removal.

The use of Koehler integration optics to achieve this effect also maintains reasonably efficient use of the available collected light, despite the increased number of optical elements which may be required in the collection optics. This can be important for many reasons. In spectrometry applications, and especially in such applications using Raman spectroscopy which has a low collision cross section, efficient use of the collected light enables exposure and integration times to be reduced (many seconds or even minutes may often be needed), probe light power to be reduced (making the laser or other light source easier or cheaper to implement with required levels of power consumption, stability and so forth, as well as reducing potential for light/heating damage to the sample), and makes achieving a desired spectral resolution and detector sensitivity easier.

Figure 2:
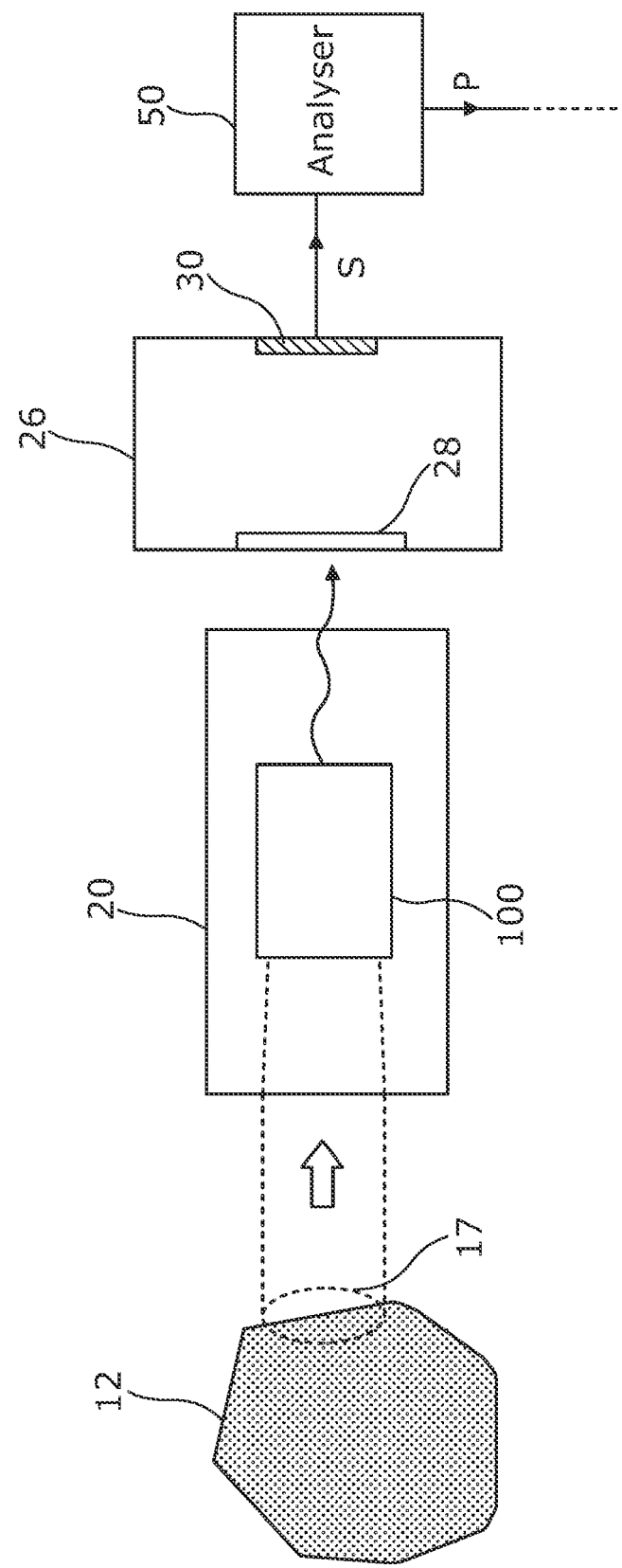
FIG. 2 shows apparatus similar to that of FIG. 1, but using a reflection geometry for probe light at the sample.

FIG. 2 illustrates some different ways in which aspects of FIG. 1 may be implemented more generally. Details of FIG. 1 and as described above may be included in the arrangement of FIG. 2 as desired. In FIG. 2 no laser light source 22 is depicted. Illumination of the sample 12 may take place using a laser light source 22 as depicted in FIG. 1 using delivery optics, but instead the light source 22 could be provided by any light source suitable for the spectrometry to be carried out, and not necessarily by a laser source. For example an LED or other broadband light source could be used with suitable filtering to achieve the required spectral narrowing for the implemented spectroscopy technique. In some cases, it may be desirable or appropriate to use ambient light, light from the sun, or other sources. If the light source is able to form a suitable beam, or if no particular beam is required for the illumination of the sample, then separate or specific delivery optics may not be required.

Whereas in FIG. 1 the sample was held by a support 40, no such support is depicted in FIG. 2, although any kind of support, carrier, holder, manipulator or other arrangement suitable for managing and retaining the sample in place may be used as desired. In some embodiments, the sample 12 may be the whole or part of an object which is to be tested in situ, for example an object in a warehouse or on a conveyor belt, or a surface in a building, or an object on a table.

Whereas in FIG. 1 a transmission geometry is used such that the probe light is directed to a delivery region 13 spaced from or opposite to the collection region 17, so that the probe light is forward scattered through a bulk of the sample before emerging for collection from the collection region 18, in FIG. 2 no particular geometry is shown. Although a transmission geometry such as that of FIG. 1 could be used, the sample may also or instead be illuminated by probe light in various other ways, for example with probe light being provided directly onto some or all of the collection region from which the collection optics collect probe light for spectral analysis in a reflection or backscattering geometry, in which case the collection and delivery regions may be described as coincident or overlapping. The probe light could be delivered to the sample along or proximal to the collection beam path, for example by using a partially reflecting or other mirror, or along some other path for example off-axis with respect to the collection path. Other geometries may include delivery of probe light at some intermediate angle between transmission and backscatter geometries, for example oblique or at right angles to the collection path, for example being directed to side walls or side portions of the sample.

As already depicted in FIG. 1, the collection optics 20 are arranged to collect probe light scattered from a collection region 17 of the sample, which may be all of the visible surface of the sample from the perspective of the collection optics, or a smaller part of the visible surface as seen in FIG. 2. Moreover, the collection region may be a single contiguous region, or could comprise two or more separate regions. Although a broadly circular collection region may be consistent with use of geometric optics in the collection optics, the collection region could have various other shapes or forms. The sample could be positioned quite close to the collection optics, or at a greater distance in which case suitable telescopic optics could be included within the collection optics.

The spectrometer 26 is arranged to receive the collected probe light from the collection optics at the entrance port 28 of the spectrometer, and to detect spectral features in the received probe light. Also as already depicted in FIG. 1, the collection optics as shown in FIG. 2 comprise Koehler integration optics 100 (or other di-imaging optics) arranged to process the collected probe light for passing to the entrance port of the spectrometer as described elsewhere in this document. An optical fibre or fibre optic bundle 32 as described in respect of FIG. 1 may be used to carry processed light from the Koehler integration optics to the spectrometer, or other optical arrangements may be used. For example, the Koehler integration optics may be arranged to direct the processed light directly onto the entrance port, optionally via one or more relays or other optical arrangements as discussed below.

As for FIG. 1, in FIG. 2 an analyser 50 is arranged to receive spectral data, comprising detected spectral feature such as peak positions and intensities, from the spectrometer 26, and to determine one or more properties of the sample 12 from the detected spectral features. Typically, the apparatus may be arranged to carry out Raman spectroscopy of the sample, so that the detected spectral features are then Raman spectral features, although other types of spectroscopy such as fluorescence, infrared absorption absorption, or visible light reflectance spectrometry may be used The Koehler integrator or Koehler integration optics 100 of FIGS. 1 and 2 can be implemented in a variety of ways known to the skilled person. However, specific technical issues related to providing light from a sample to a spectrometer have prompted the inventors to consider a number of particular arrangements which address some of those needs.

Figure 3:
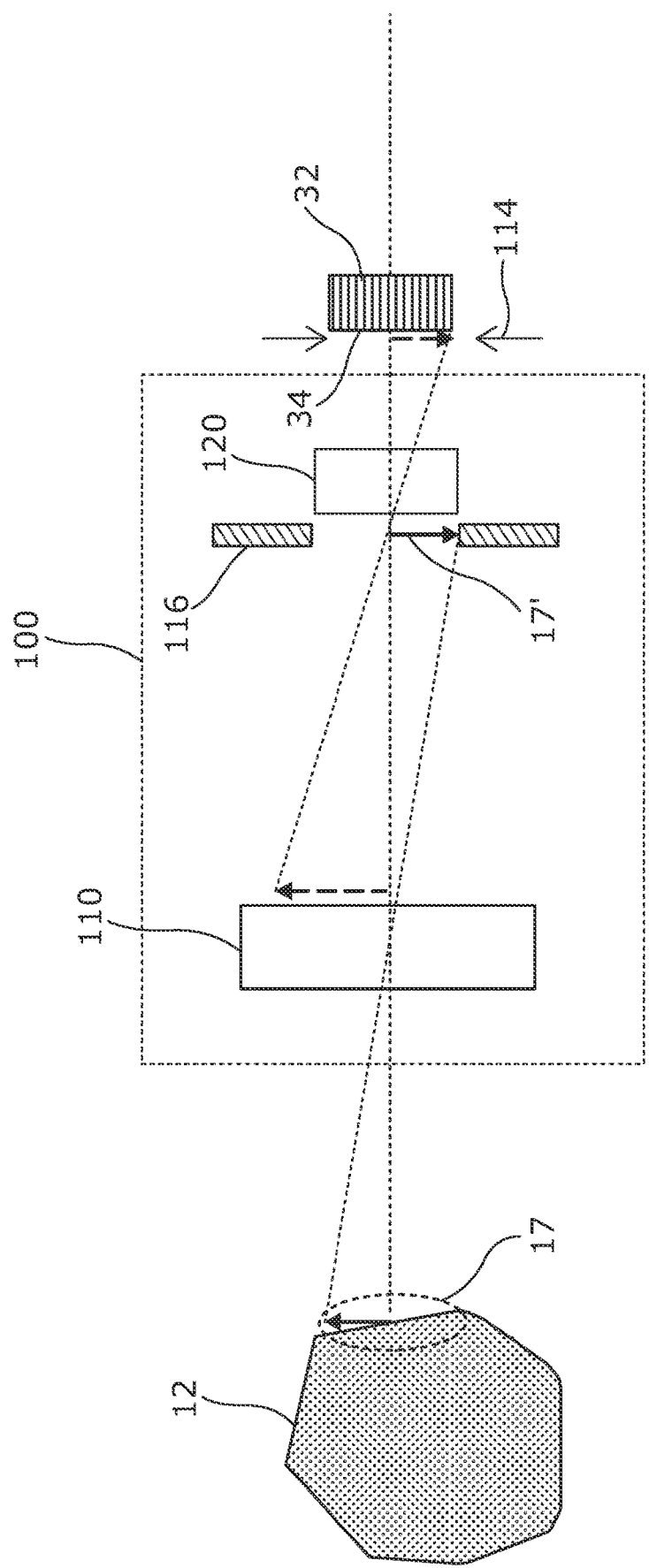
FIG. 3 shows one way in which the Koehler integration optics of FIGS. 1 and 2 may be implemented.

To this end, various ways in which the Koehler integration optics 100 of FIGS. 1 and 2 may be implemented will now be described. In FIG. 3 the Koehler integration optics 100 comprise a collector 110 and a condenser 120. The collector 110 is arranged to receive probe light which is scattered from the collection region 17 at the sample 12. Although in FIG. 3 the collector 110 receives the collected light directly from the collection region 17, this may take place instead via one or more other optical elements or devices, such as a telescope, a relay, one or more mirrors, and so forth (not shown). The collector 110 is arranged to form a virtual image 17' of the collection region at or proximal to the condenser 120.

The condenser 120, in turn, is arranged to form an image, typically also a virtual image, at an output plane of the 114 of the Koehler integration optics. The image formed at the output plane 114 is an image of an intermediate plane 112 which is located at or proximal to the collector 110. In FIG. 3 the output plane 114 is located at or proximal to the entry face 34 of the fibre optic bundle 32 depicted in FIG. 1. However, the output plane could instead be a plane used as an input plane to a relay or other further optics which in turn images the output plane onto the entry face 34 of the fibre optic bundle, or the condenser 120 or further relay or other optics could form an image of the intermediate plane at or proximal to the entry port 28 of the spectrometer itself.

The Koehler integration optics 100 may be provided with a condenser diaphragm 116 located at, or just ahead of the condenser 120, which may serve to limit the size of the virtual image 17' of the collection region formed at the condenser and to exclude unwanted light from degrading the image of the intermediate plane which is formed at the output plane. To this end, the condenser diaphragm 116 may be used to define the perimeter of the virtual image 17' of the collection region 17 formed at or proximal to the condenser, thereby assisting in defining the effective extent of the collection region itself, although this may additionally or alternatively be defined by other diaphragms within the collection optics 20.

The collector 110 and condenser 120, and other optical elements of the Koehler integration optics may each be provided by single lenses, compound lenses, or combinations of such single and/or compound lenses, each of which may be of spherical or aspherical form according to the detail of the design.

In a typical implementation, the focal length and optical diameter of the collector 110 may be around 25 mm and 15 mm respectively. In order to effectively input the collected light into the fibre optic bundle with high effective aperture, the focal length and optical diameter of the condenser 120 may be much smaller, for example around 3 mm and 3 mm respectively, giving an effective numerical aperture of about 2.5.

Depending on the type of spectroscopy implemented by the apparatus 10, it may be desirable to include one or more spectral filters within the collection optics 20, and conveniently within the Koehler integration optics. For example, if the apparatus is to carry out Raman spectroscopy of the sample, then typically it will be very desirable to provide one or more spectral filters which exclude the wavelengths of the original laser light from entering the spectrometer but permit the Raman scattered wavelengths of interest to pass. For such purposes, notch filters or more usually low pass filters which exclude the original laser light may be used, although various other types of spectral filter may be used depending on the circumstances.

Typically, such spectral filters may be of holographic or dielectric (multilayer) types, whereby the spectral properties of the filter are somewhat dependent upon the angle of incidence of light at the filter, so that arranging such filters in a region of the collection optics where the light is reasonably well collimated can be important to avoid spectral and other artefacts being introduced. Moreover, if two or more such filters are used, they typically function more effectively if spaced further apart, for example by a distance of around the diameter of each filter or more.

To this end the collection optics 20 may comprise one or more groups of collimator lenses and one or more spectral filters disposed within each group of collimator lenses, each group of collimator lenses being arranged such that the collected light is at least partly collimated when passing through the one or more spectral filters disposed within the group. The degree of collimation required may typically need to be to within about 2 to 3 degrees from the optical axis in order to largely avoid the undesirable effects of non-collimation, although other amounts of collimation may be used depending on the design constraints of the particular apparatus, for example within about 5 degrees.

Figure 4:
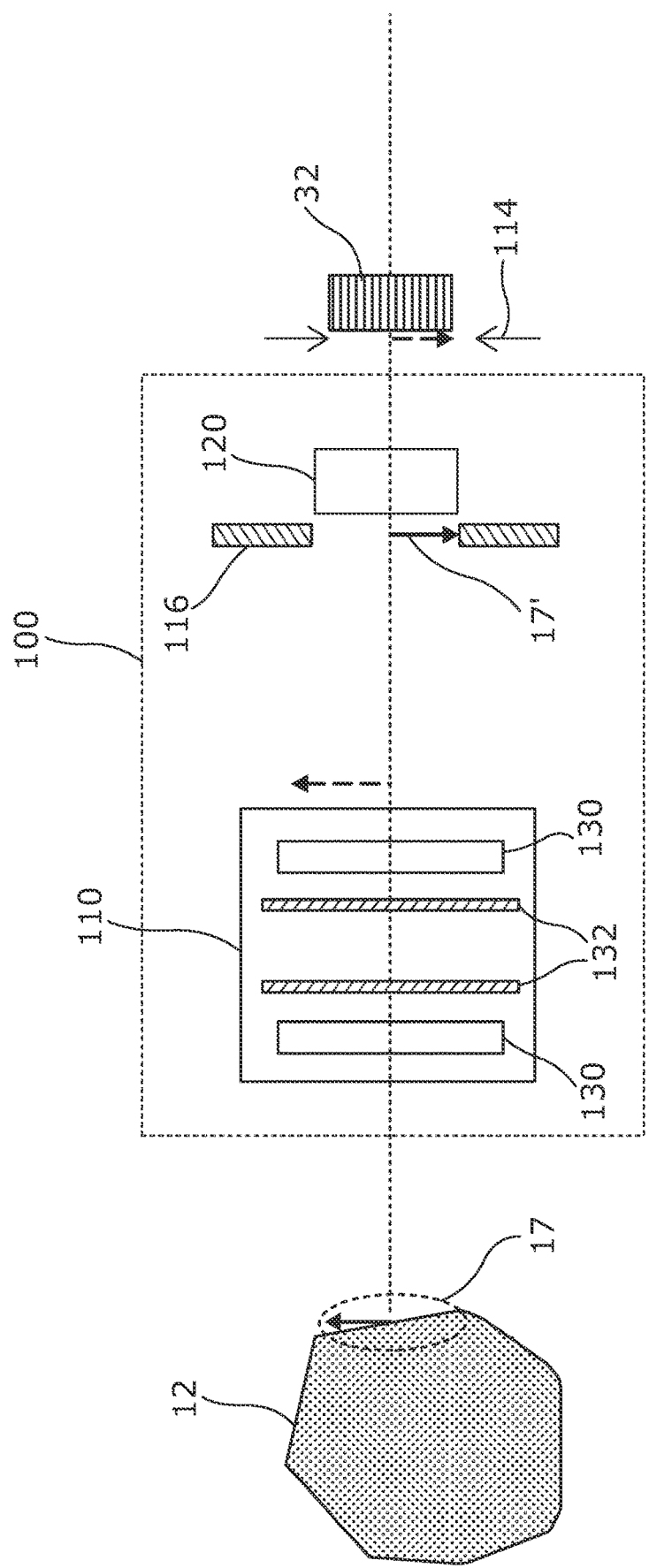
FIG. 4 is similar to FIG. 3 with the collector including collimating lenses and spectral filters.

FIG. 4 shows an adaptation of the arrangement of FIG. 3 in which a group of collimator lenses is formed using collimator lenses 130 comprised in the collector 110, and one or more said spectral filters 132 are also comprised within the collector, located between the collimator lenses 130. Using this arrangement the collector both functions to form a virtual image of the collection region at the condenser 120 or condenser diaphragm 116, and to provide adequate collimation of the light within the collector 130 to permit spectral filters 132 to perform their function sufficiently well.

In the arrangement of FIG. 4, the collector 110 may therefore be implemented using a pair of simple or compound collimator lenses 130, with the one or more spectral filters located between the lenses. Each of the collimator lenses may for example have a focal length of about 30 mm and an optical diameter of about 25 mm, and the collimator lenses may be typically spaced by about 100 mm in order to provide adequate space for the spectral filters 132 to operate effectively.

Figure 5:
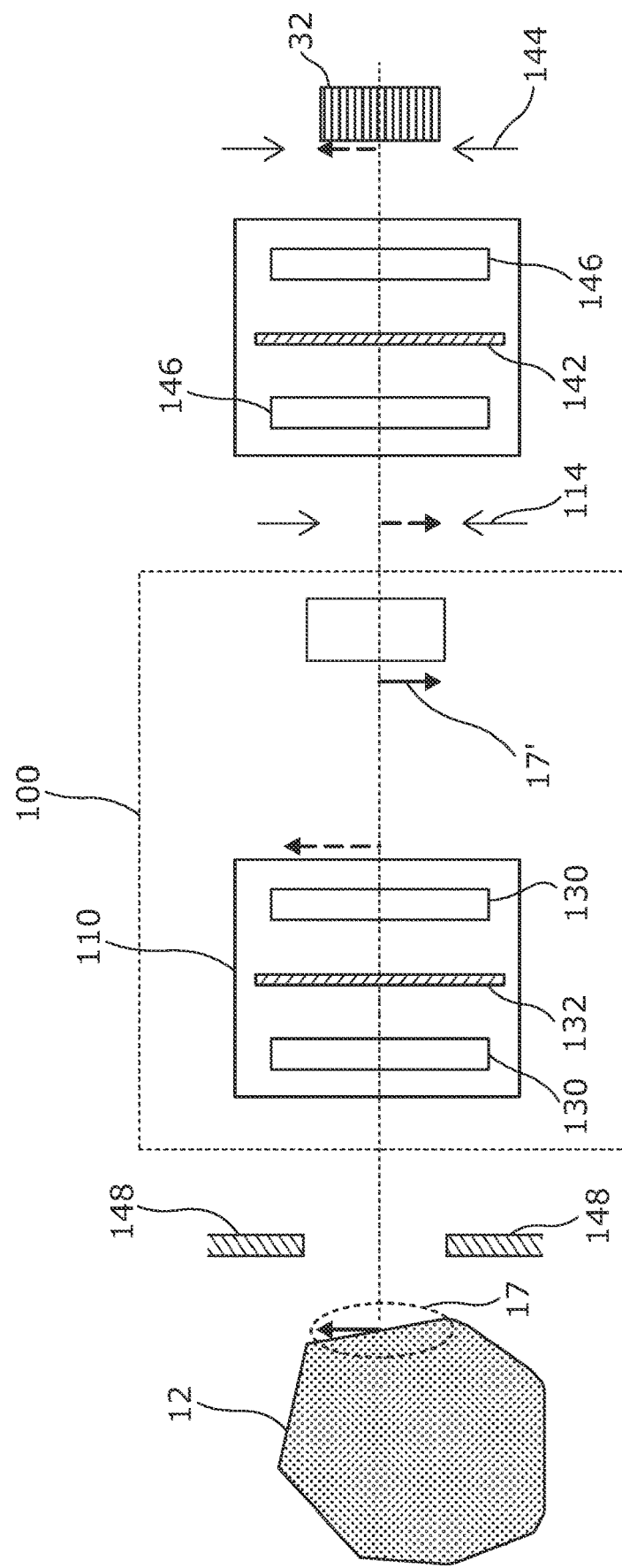
FIG. 5 is similar to FIG. 3 with the addition of an output relay used to include spectral filters after the Koehler integration optics.

If two or more spectral filters are to be used, then the arrangement of FIG. 4 tends to extend the length of the Koehler integration optics more than may be desirable in order to keep an adequate separation between the spectral filters. FIG. 5 shows an adaptation of the arrangements of FIGS. 4 and 5 in which one, or potentially more than one, spectral filter 132 is optionally comprised within the collector, for example between collimator lenses 130 comprised in the collector 110, and one or more further spectral filters 142 are comprised within an output relay 140 which is arranged to relay the output plane 114 of the Koehler integration optics on to a second output plane 144, which could be located at the entry face 34 of the optical fibre bundle 32 as shown in the figure, or directly at the entrance port 28 of the spectrometer. The output relay may for example comprise a pair of collimation lenses 146 with the one or more further spectral filters 142 located between these collimation lenses. This arrangement permits greater separation of the spectral filters 132, 142, although achieving adequate collimation of the light within the output relay may be difficult to achieve alongside a reasonably high numerical aperture into the second output plane 144.

The arrangement of FIG. 5 also lacks the condenser diaphragm seen in FIGS. 3 and 4, so absent some other arrangement for limiting the collection region such as an aperture proximal to the sample itself, the one or more spectral filters 132 within the collector 110 may allow a significant amount of high angle of incidence laser wavelength light arising from various surfaces in the collection optics (such as lens edges or anodised surfaces) to scatter on through the system. To this end, in FIG. 5 an optional sample diaphragm 148 is located proximally to the sample 12, to help prevent stray probe light from outside of the collection region 17 from entering the collection optics.

Use of a sample diaphragm 148 or other arrangement close to the sample to block unwanted probe light is inconvenient or undesirable in a particular implementation, for example if the sample is being held by a manipulator in free space in front of the collection optics 20. To this end, FIG. 6 shows a further adaptation which can be applied to any of the previous arrangements, in which the sample diaphragm 148 is separated from the sample by a sample relay 150 which is arranged to form a virtual image of the sample 12 at the sample diaphragm 148, which thereby assists in defining the scope of the collection region 17 on the sample 12 and prevents further propagation of light from outside the collection region through the collection optics.

The sample relay 150 may constructed in a similar manner to the output relay 140 discussed above in connection with FIG. 5, for example comprising a pair of collimation lenses 156 and one or more spectral filters 152 located between the collimation lenses. However, in other embodiments a single simple or compound lens could be used to provide the sample relay 150. Similarly, in FIG. 6 the collector 110 is illustrated as comprising a pair of collimation lenses 130, and one or more spectral filters 132 located between the collimation lenses, but a single simple or compound lens could instead be used.

Figure 6:
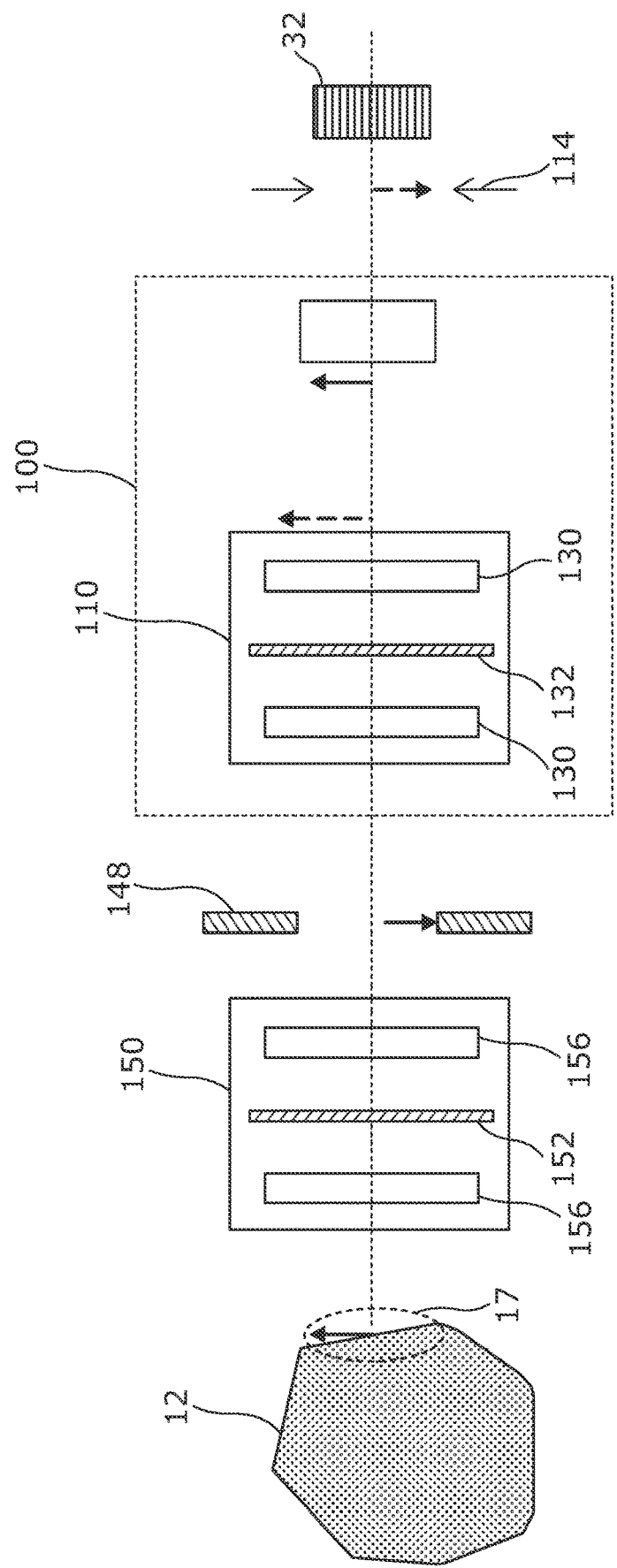
FIG. 6 is similar to FIG. 3 with the addition of a sample relay ahead of the Koehler integration optics.

In an example embodiment corresponding to FIG. 6, the first collimation lens 156 of the sample relay 150 may have focal length of about 60 mm to provide a desired spacing from the sample, and an optical diameter of about 25 mm, and the second collimation lens may have a focal length of about 35 mm and an optical diameter of about 25 mm. The first and second collimation lenses 130 of the collector 110 may then each have a focal length of about 30 mm and a diameter of about 25 mm, and the single lens of the condenser may have a focal length and a diameter of about 3 mm, with these small values being used in order to provide a sufficiently high numerical aperture of around 2.5 at the output plane 114 for coupling (via a further relay if desired) into the optical fibre bundle or directly into the entrance port of the spectrometer.

The Koehler integration optics generally shown in FIGS. 1 and 2 can be implemented in various other ways. Using conventional, single aperture lenses in the collector and condenser can lead to minor deviations, in an approximately Gaussian distribution, of light intensity across the output plane. Such effects can be mitigated using an arrangement such as that shown in FIG. 7 in which the collector 110 comprises a collector lenslet array 170, and the condenser 120 comprises a condenser lenslet array 172. The two lenslet arrays are matched so that each lenslet of one array corresponds to one of the other array, the arrays typically being of the same size and optical properties. More particularly the two lenslet arrays may be co-focal, so that each lenslet of each array is at or close to the focal point of a corresponding lenslet of the other array. In effect, the lenslet arrays 170, 172 subsample the apertures of the collector and condenser, and these subsamples are then superimposed again at the output plane 114, providing additional mixing of different parts of the collection region onto the output plane.

Typically, the collector lenslet array 170 may follow a collector lens 174 within the collector 110, so as to subsample the aperture of the collector lens 174, and the condenser lenslet array 172 may similarly precede a condenser lens 176 in the condenser. One or more spectral filters 178 may be provided in one or both of the collector 110 and condenser 120, preferably before the lenslet array in the collector, and/or after the lenslet array in the condenser as shown in FIG. 7.

The matched lenslet arrays may be rectilinear arrays of, for example, 3×3 to 5×5 lenslets. Using more lenslets in each array provides for increased performance in terms of subsampling the aperture and overlaying the subsamples at the output plane, but because accurate alignment of the lenslets is important in order to maintain light throughput, increasing the number of lenslets further may make construction more difficult. The lenslet arrays could instead be hexagonally packed or otherwise arranged, typically comprising between about 5 and 30 lenslets.

Figure 7:
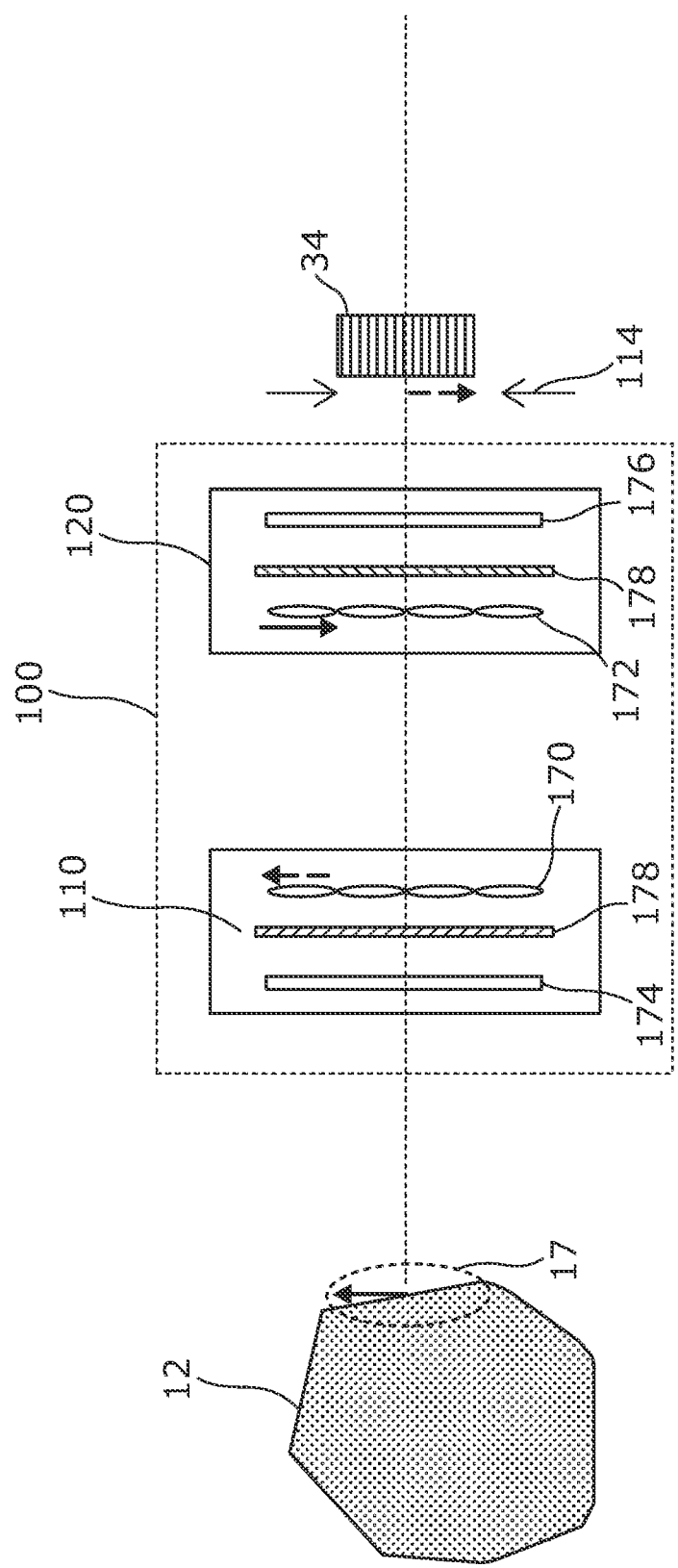
FIG. 7 shows how the Koehler integration optics may be implemented using lenslet arrays.

The lenslet array arrangements illustrated in FIG. 7 may be combined with various other construction details already discussed above. If an output relay as depicted in FIG. 5 is used with the lenslet arrangement, then it may be desirable to include an output plane diaphragm at the output plane 114 ahead of the output relay, which may include one or more spectral filters as discussed above. A sample relay as depicted in FIG. 6 may also or instead be used in combination with the described lenslet arrays, implementing one or both of the sample aperture 148 between the sample relay and the collector, and the spectral filters 152 within the sample relay.

Figure 8:
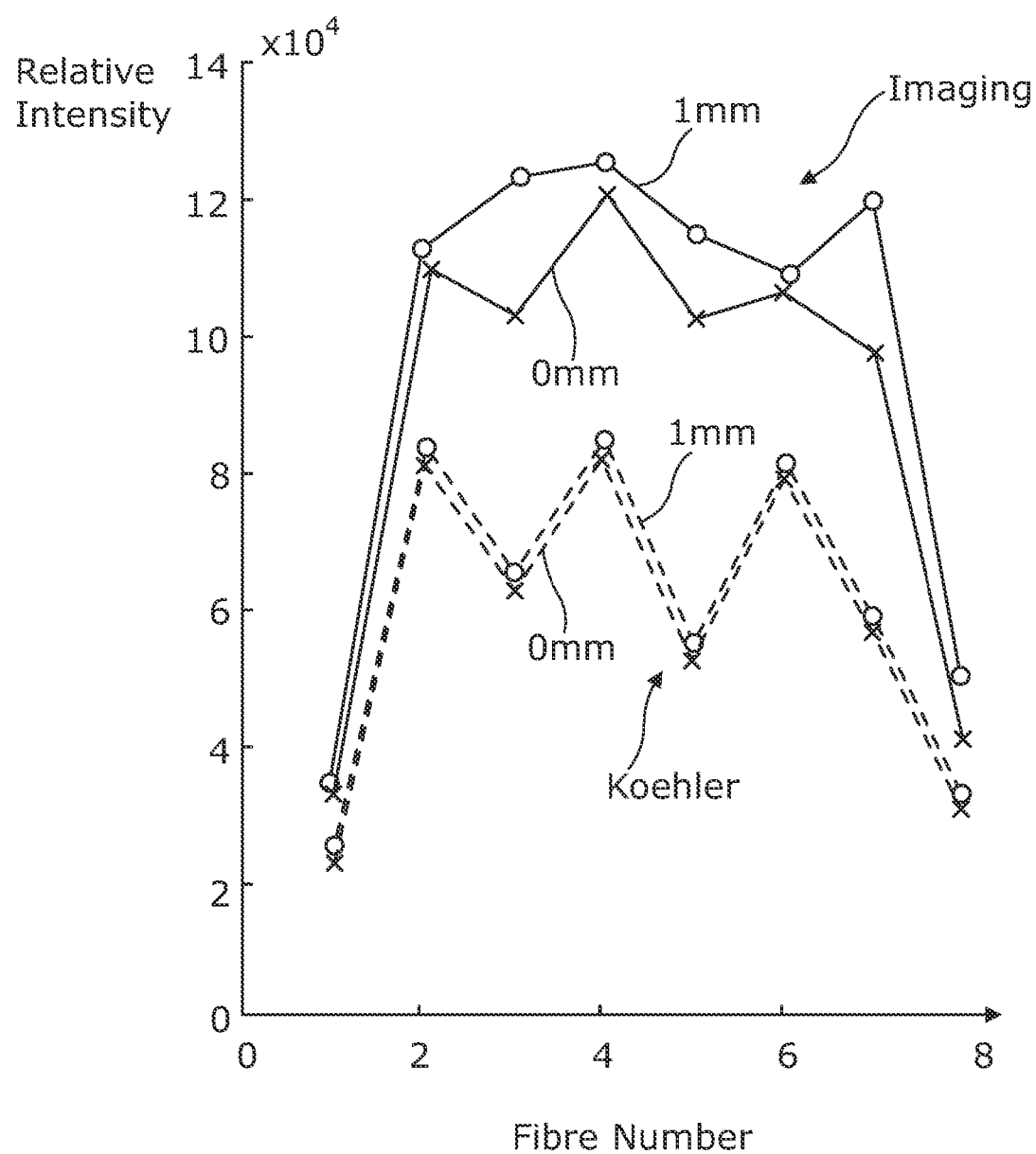
FIG. 8 is a graph of intensities across fibres of an optical fibre bundle under slight movement of the sample, with and without the use of Koehler integration optics.

FIG. 8 depicts results of using an arrangement similar to that of FIGS. 1 and 3 to sample light from a collection region of a pharmaceutical tablet (a Trazadone® tablet was used), during illumination of the opposite side of the tablet using infrared laser light. Collection optics 20 comprising Koehler integration optics 100 similar to those of FIG. 3 included an optical fibre bundle, and the Koehler integration optics 100 were arranged to process light from a collection region of the tablet and to direct the processed light onto an entry face 32 of the bundle. Then, instead of coupling the other end of the optical fibre bundle to the spectrometer, light intensity emerging from each optical fibre at the exit face 36 was measured.

Notably, the collection optics were arranged such that the Koehler integration optics could be included in or excluded from the collection of the light from the tablet, without any change in the shape or size of the collection region. This was achieved by ensuring that the collection area in both cases had equivalent illuminations so that the capturable photon flux remained the same. When the Koehler integration optics were excluded, in an "imaging" mode the collection optics formed an image of the collection region 17 directly onto the entry face 32 of the bundle.

In more detail, FIG. 8 presents a graph in which the x-axis corresponds to each of the eight optical fibres present in the bundle, and the y-axis to the detected intensity of light (in arbitrary units) emerging from each optical fibre at the exit face 36. Each of the two solid lines depicts the measured intensities, without Koehler integration optics being used (imaging mode), when the collection region was aligned accurately with a centre of the tablet (labelled "0 mm" and points as "x"), and the second when the collection region was moved a small distance of 1 mm away from this position (labelled "1 mm" and points as "o"). The broken lines depict the corresponding measurements with the Koehler integration optics being used (Koehler mode).

It can be seen that, although there is a significant loss of overall intensity when the Koehler integration optics are being used, there is a very high degree of consistency in the intensity of light being measured at any one of the optical fibres between the two collection region positions. When the Koehler integration optics are not used, there is quite a large degree of variation in the intensity at each fibre resulting from even the present very small amount of movement of the collection region, and moreover, this degree of variation is high variable from fibre to fibre.

Note that in the present experiment, even for use of the Koehler integration optics, there is a significant amount of variation in the intensity seen from one optical fibre to the next. This variation was probably due to use of off-the-shelf and non-optimised lenses with a degree of mechanical misalignment, so could easily be improved. However, because this variation is a constant effect it does not impact on the consistency of spectroscopic measurements from one sample to another.

The experiment illustrated in FIG. 8 was repeated for a larger number of Trazadone tablets, twenty seven in all, and at a plurality of different offset positions and orientations relative to the collection optics for each tablet, with similar results demonstrating that although there was notable loss of intensity in each optical fibre, the consistency of intensity at each fibre under movement of the tablet and of using different tablets was improved by a factor of around ten by using the Koehler integration optics.

Figure 9:
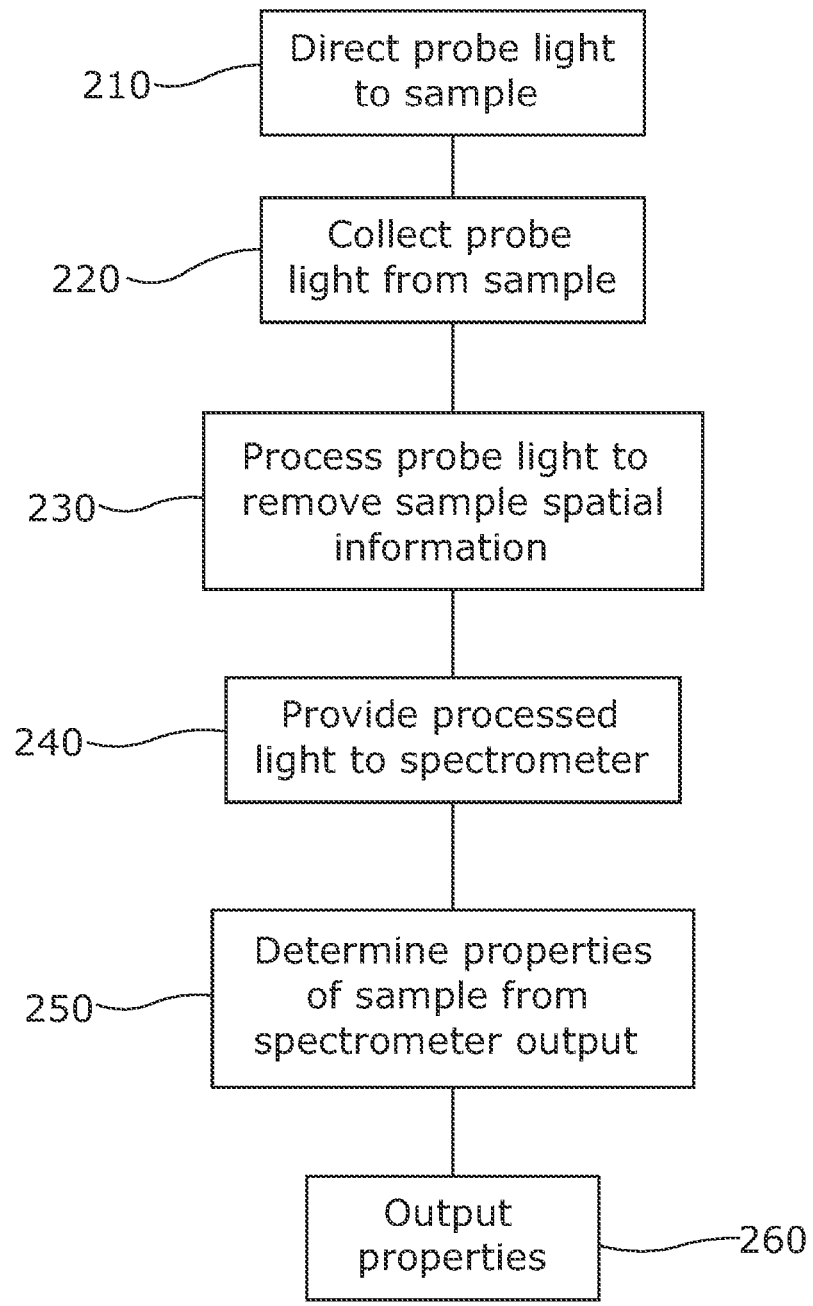
FIG. 9 illustrates a method according to the invention.

The invention provides methods of constructing and methods of operating apparatus which is described herein, and corresponding methods of carrying out analysis of one or more samples. FIG. 9 illustrates such a method, but any of the process steps and operations discussed above may be implemented in such a method.

In a first step 210 of FIG. 9, probe light is directed to the sample 12. The probe light may be laser probe light, or some other probe light suitable for carrying out the desired spectroscopy as discussed above. Probe light scattered from the sample 12 is then collected at step 220. The collection of probe light may be arranged such that the probe light has been forward scattered through the sample (in a transmission geometry) or in other ways as discussed above. The scattering may involve various spectral processes such as Raman scattering, infrared absorption and so forth.

At step 230 the collected probe light is processed to remove some or all of the spatial information arising from the sample. This may be described as removing image information in respect of a collection region of the sample, or in other ways as set out above, and in particular Koehler integration may be used for this process. Typically during this process, light from each point of the collection region on the sample is mixed with the light from other points of the collection region, so as to be distributed across some or all of the output of the process.

The processed collected light is then passed to a spectrometer at step 230, and the spectrometer is used to detect spectral features of the collected light. Typically, the processed light may be passed to an extended entrance port such as a slit of the spectrometer, which may typically be a dispersive spectrometer implemented using a diffraction grating or similar. Because such spectrometers are susceptible to slight variations in wavelength response or calibration along the entrance port or slit, providing collected light from which spatial information of the sample has been removed improves consistency of spectral response of the apparatus under slight movements or geometric variations of the sample.

Spectral features output by the spectrometer, such as a full or part spectrum, or properties of individual features such as one or more particular peak intensities, are then used at step 250 to determine one or more properties of the sample, such as presence or a measurement of one or more chemical components. Such properties, or information relating to such properties such as an alarm indicating a property falls outside a desired range, are output at step 260.

Some aspects of the described apparatus and methods may be implemented using computer program code executing on one or more suitable computer systems. Such computer systems will typically comprise one or more microprocessors to execute such computer program code, memory to store such programs and related data, and suitable input and output facilities which may include for example wired or wireless data connections, non-volatile storage, as well as visual displays, and input device such as keyboards and mice if required.

The analyser 50 for example, as depicted in FIGS. 1 and 2 may comprise one or more suitable computer systems programmed with suitable software to receive Raman spectral features S from the spectrometer 26, analyse and process those spectral features in various ways for example to reduce noise, transform into desired forms, and measure particular spectral features, and to match particular spectral features with those of known or expected components or characteristics of the sample under test in order to determine properties P of the sample. Libraries of spectral features which may be used for such comparisons are available for example from S.T. Japan or Sigma-Aldrich.

Although various embodiments of the invention have been described, the skilled person will be aware that a number of different modifications and changes to those embodiments may be made without departing from the scope of the invention.

The invention claimed is:

1. Apparatus for spectral analysis of a sample, wherein the sample is a pharmaceutical dosage form, comprising:
   delivery optics arranged to direct probe light to a delivery region of the sample;
   collection optics arranged to collect probe light scattered from a collection region of the sample; and
   a spectrometer having an entrance port, the spectrometer being arranged to receive the collected probe light from the collection optics at the entrance port of the spectrometer, and to detect spectral features in the received probe light,
   wherein the collection optics comprise Koehler integration optics arranged to process the collected probe light,
   wherein the collection optics comprises a bundle of optical fibres having an entry face arranged to receive the collected probe light following processing by the Koehler integration optics, and an exit face arranged to deliver the collected probe light to the port of the spectrometer,
   whereby the Koehler integration optics collect and process the scattered light such that the collected light from each point of the collection region is distributed across the entrance port of the spectrometer.

2. The apparatus of claim 1 further comprising an analyser arranged to determine one or more properties of the sample from the detected spectral features.

3. The apparatus of claim 1 wherein the detected spectral features are Raman spectral features.

4. The apparatus of claim 1 wherein the collection region is spaced from the delivery region.

5. The apparatus of claim 4 wherein the collection region is on an opposite side of the sample from the delivery region.

6. The apparatus of claim 1 wherein the Koehler integration optics comprises a collector arranged to receive the collected light from the collection region of the sample, and a condenser arranged to receive the collected light from the collector.

7. The apparatus of claim 6 wherein the Koehler integration optics define an intermediate plane at or proximal to the collector, and an output plane, the collector being arranged to form an image of the collection region of the sample at or proximal to the condenser, and the condenser being arranged to form an image of the intermediate plane at the output plane.

8. The apparatus of claim 7 wherein the collection optics comprises a bundle of optical fibres, the bundle having an entry face arranged to receive the collected probe light following processing by the Koehler integration optics, and an exit face arranged to deliver the collected probe light to the port of the spectrometer, and wherein the output plane is located at or proximal to the entry face.

9. The apparatus of claim 6 wherein collection optics comprises one or more groups of collimator lenses and one or more spectral filters disposed within each group of collimator lenses, each group of collimator lenses being arranged such that the collected light is collimated when passing through the one or more spectral filters disposed within the group.

10. The apparatus of claim 9 wherein a said group of collimator lenses are lenses of the collector and one or more said spectral filters are comprised within the collector.

11. The apparatus of claim 9 wherein a said group of collimator lenses are comprised in an output relay arranged to relay an image of the output plane from the condenser, and one or more said spectral filters are comprised within the output relay.

12. The apparatus of claim 9 wherein a said group of collimator lenses are comprised in a sample relay arranged to form a relayed virtual image of the collection region for imaging by the collector, and one or more said spectral filters are comprised within the sample relay.

13. The apparatus of claim 12 further comprising a sample diaphragm between the sample relay and the collector, the sample relay being arranged to form the relayed virtual image of the collection region at the sample diaphragm.

14. The apparatus of claim 9 wherein the detected spectral features are Raman spectral features, the probe light directed to the delivery region of the sample has one or more probe wavelengths, and the one or more spectral filters comprise spectral filters arranged to block light of the probe wavelengths but to allow light of the Raman spectral features to pass.

15. The apparatus of claim 6 further comprising a sample diaphragm, and a sample relay arranged to form a relayed virtual image of the collection region at the sample diaphragm for imaging by the collector.

16. The apparatus of claim 6 further comprising a condenser diaphragm at or proximal to the condenser, such that the condenser diaphragm constrains the extent of the virtual image of the collection region formed by the collector at or proximal to the condenser.

17. The apparatus of claim 6 wherein the collector comprises a collector lenslet array, the condenser comprises a condenser lenslet array.

18. The apparatus of claim 17 wherein the collector and condenser lenslet arrays are co-focal, such that the lenslet arrays subsample the apertures of the collector and condenser and the subsamples are superimposed at the output plane.

19. A method of spectral analysis of a sample, wherein the sample is a pharmaceutical dosage form, comprising:
   directing probe light to a delivery region of the sample;
   collecting probe light from a collection region of the sample;
   processing the collected probe light by Koehler integration optics such that the collected light from each point of the collection region is distributed across an entrance port of a spectrometer by receiving the collected probe light at an entry face of a bundle of optical fibres arranged following processing by the Koehler integration optics; and
   delivering the processed collected probe light from an exit face of the bundle of optical fibres to the entrance port of the spectrometer.

* * * * *